United States Patent
Evans et al.

(10) Patent No.: US 10,881,476 B2
(45) Date of Patent: Jan. 5, 2021

(54) DRIVE CABLE CAPSTANS FOR ROBOTIC SURGICAL TOOLS

(71) Applicant: Ethicon LLC, Guaynabo, PR (US)

(72) Inventors: John Evans, Appleton, WI (US); Robbie Loehr, Durham, NC (US)

(73) Assignee: Ethicon LLC, Guaynabo, PR (US)

( * ) Notice: Subject to any disclaimer, the term of this patent is extended or adjusted under 35 U.S.C. 154(b) by 462 days.

(21) Appl. No.: 15/794,519

(22) Filed: Oct. 26, 2017

(65) Prior Publication Data

US 2019/0125465 A1 May 2, 2019

(51) Int. Cl.
*A61B 34/00* (2016.01)
*A61B 34/37* (2016.01)
*A61B 34/30* (2016.01)
*A61B 17/00* (2006.01)
*A61B 17/32* (2006.01)

(52) U.S. Cl.
CPC ........ *A61B 34/71* (2016.02); *A61B 17/00234* (2013.01); *A61B 34/30* (2016.02); *A61B 34/37* (2016.02); *A61B 34/70* (2016.02); *A61B 34/74* (2016.02); *A61B 34/75* (2016.02); *A61B 34/77* (2016.02); *A61B 2017/320032* (2013.01); *A61B 2034/305* (2016.02)

(58) Field of Classification Search
CPC combination set(s) only.
See application file for complete search history.

(56) References Cited

U.S. PATENT DOCUMENTS 8,831,782 B2 9/2014 Itkowitz
9,050,120 B2 * 6/2015 Swarup ................. A61B 34/37
2002/0087049 A1 7/2002 Brock et al.
2007/0142969 A1 * 6/2007 Devengenzo ...... A61B 1/00149
700/245
2009/0088774 A1 * 4/2009 Swarup .................. A61B 34/30
606/130
2011/0313405 A1 12/2011 Anderson et al.
(Continued)

FOREIGN PATENT DOCUMENTS

| EP | 3112097 A1 | 1/2017 |
|----|-----------|--------|
| WO | 2014/151621 | 9/2014 |
| WO | 2014/151952 | 9/2014 |

OTHER PUBLICATIONS

International Search Report and Written Opinion received in corresponding PCT application No. PCT/US2018/056411 completed Jul. 4, 2019 and dated Jul. 16, 2019.

*Primary Examiner* — Michael W Kahelin
*Assistant Examiner* — Shirley X Jian
(74) *Attorney, Agent, or Firm* — Vorys, Sater, Seymour and Pease LLP

(57) ABSTRACT

A surgical tool includes a drive housing having an input shaft and a drive cable capstan arranged therein. The input shaft includes a drive gear and the drive cable capstan including a driven gear intermeshed with the drive gear such that rotation of the input shaft rotates the drive cable capstan. An elongate shaft extends from the drive housing, and an end effector is operatively coupled to a distal end of the elongate shaft. A drive cable is received within a pulley track defined on the drive cable capstan and extends only partially around a circumference of the drive cable capstan. The drive cable is fed directly into the elongate shaft from the pulley track and extends to the end effector.

21 Claims, 11 Drawing Sheets

(56) References Cited

U.S. PATENT DOCUMENTS

| | | |
|---|---|---|
| 2014/0005681 A1 | 1/2014 | Gee et al. |
| 2015/0313676 A1 | 11/2015 | Deodhar |
| 2016/0287252 A1 | 10/2016 | Parihar |
| 2016/0338788 A1 | 11/2016 | Hares |

* cited by examiner

DRIVE CABLE CAPSTANS FOR ROBOTIC SURGICAL TOOLS

BACKGROUND

Minimally invasive surgical (MIS) instruments are often preferred over traditional open surgical devices due to reduced post-operative recovery time and minimal scarring. Endoscopic surgery is one type of MIS procedure in which an elongate flexible shaft is introduced into the body of a patient through a natural orifice. Laparoscopic surgery is another type of MIS procedure in which one or more small incisions are formed in the abdomen of a patient and a trocar is inserted through the incision to form a pathway that provides access to the abdominal cavity. Through the trocar, a variety of instruments and surgical tools can be introduced into the abdominal cavity. The trocar also helps facilitate insufflation to elevate the abdominal wall above the organs. The instruments and tools introduced into the abdominal cavity via the trocar can be used to engage and/or treat tissue in a number of ways to achieve a diagnostic or therapeutic effect.

Various robotic systems have recently been developed to assist in MIS procedures. Robotic systems can allow for more intuitive hand movements by maintaining natural eye-hand axis. Robotic systems can also allow for more degrees of freedom in movement by including a "wrist" joint that creates a more natural hand-like articulation. The instrument's end effector can be articulated (moved) using a cable driven motion system having one or more drive cables that extend through the wrist joint.

A user (e.g., a surgeon) is able to remotely operate an instrument's end effector by grasping and manipulating in space one or more controllers that communicate with a tool driver coupled to the surgical instrument. User inputs are processed by a computer system incorporated into the robotic surgical system and the tool driver responds by actuating the cable driven motion system and, more particularly, the drive cables. Moving the drive cables articulates the end effector to desired positions and configurations. A number of mechanical and manufacturing hurdles must be overcome through component design and assembly to enable consistent and predictable performance of the end effector and its associated cable driven motion system.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure is related to robotic surgical systems and, more particularly, to improved cable driven motion systems having a rotatable drive cable capstan that feeds a drive cable from a single plane pulley track.

Embodiments discussed herein describe novel designs and improvements to drive cable capstans for robotic surgical tools. In one example of a drive cable capstan, a drive cable wraps only partially around the drive cable capstan and is fed directly into an elongate shaft of a surgical tool from the pulley track. This may prove advantageous in limiting cable derailment risks to only a single location. Moreover, feeding the drive cable directly into the elongate shaft from the drive cable capstan may eliminate the need for any idler pulleys. In some embodiments, the pulley track is defined on the drive cable capstan in a single plane, which eliminates minor changes in the overall path length of the drive cable and helps mitigate cable derailment risk.

Figure 1:
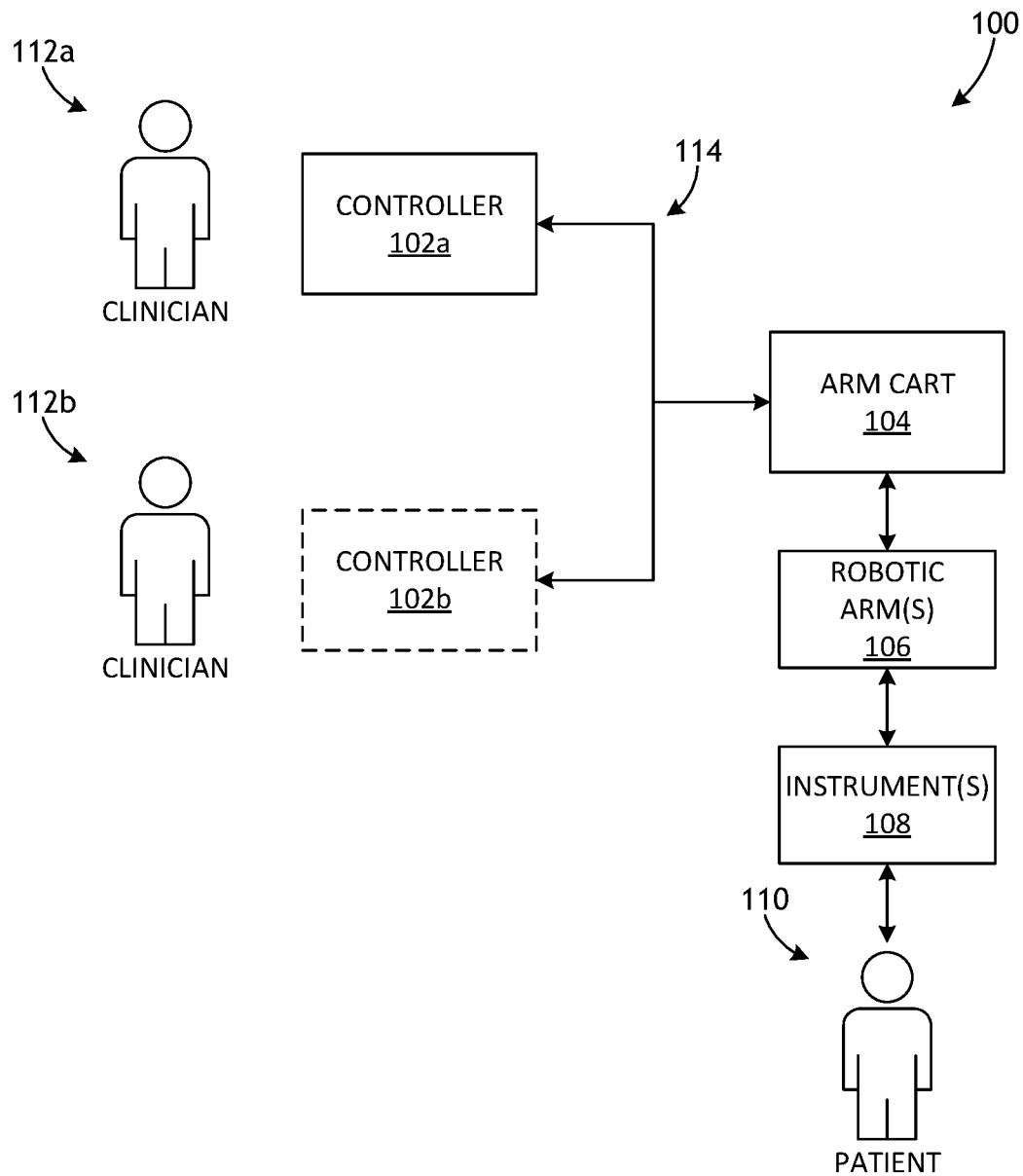
FIG. 1 is a block diagram of an example robotic surgical system that may incorporate some or all of the principles of the present disclosure.

FIGS. 1-5 illustrate the structure and operation of example robotic surgical systems and components thereof. FIG. 1 is a block diagram of an example robotic surgical system 100 that may incorporate some or all of the principles of the present disclosure. As illustrated, the system 100 can include at least one master controller 102a and at least one arm cart 104. The arm cart 104 may be mechanically and/or electrically coupled to one or more robotic arms 106, alternately referred to as "tool drivers". Each robotic arm 106 may include and otherwise mount one or more surgical tools or instruments 108 for performing various surgical tasks on a patient 110. Operation of the arm cart 104, including the arms 106 and instruments 108 may be directed by a clinician 112a (e.g., a surgeon) from the master controller 102a.

In some embodiments, a second master controller 102b (shown in dashed lines) operated by a second clinician 112b may also direct operation of the arm cart 104 in conjunction with the first clinician 112a. In such embodiments, for example, each clinician 102a,b may control different arms 106 of the arm cart 104 or, in some cases, complete control of the arm cart 104 may be passed between the clinicians 102a,b. In some embodiments, additional arm carts (not shown) may be utilized on the patient 110, and these additional arm carts may be controlled by one or more of the master controllers 102a,b.

The arm cart(s) 104 and the master controllers 102a,b may be in communication with one another via a communications link 114, which may be any type of wired or wireless communications link configured to carry suitable types of signals (e.g., electrical, optical, infrared, etc.) according to any communications protocol. The communications link 114 may be an actual physical link or it may be a logical link that uses one or more actual physical links. When the link is a logical link the type of physical link may be a data link, uplink, downlink, fiber optic link, point-to-point link, for example, as is well known in the computer networking art to refer to the communications facilities that connect nodes of a network. Example implementations of robotic surgical systems, such as the system 100, are disclosed in U.S. Pat. No. 7,524,320, the contents of which are incorporated herein by reference. The various particularities of such devices will not be described in detail herein beyond that which may be necessary to understand various embodiments and forms of the various embodiments of robotic surgery apparatus, systems, and methods disclosed herein.

Figure 2:
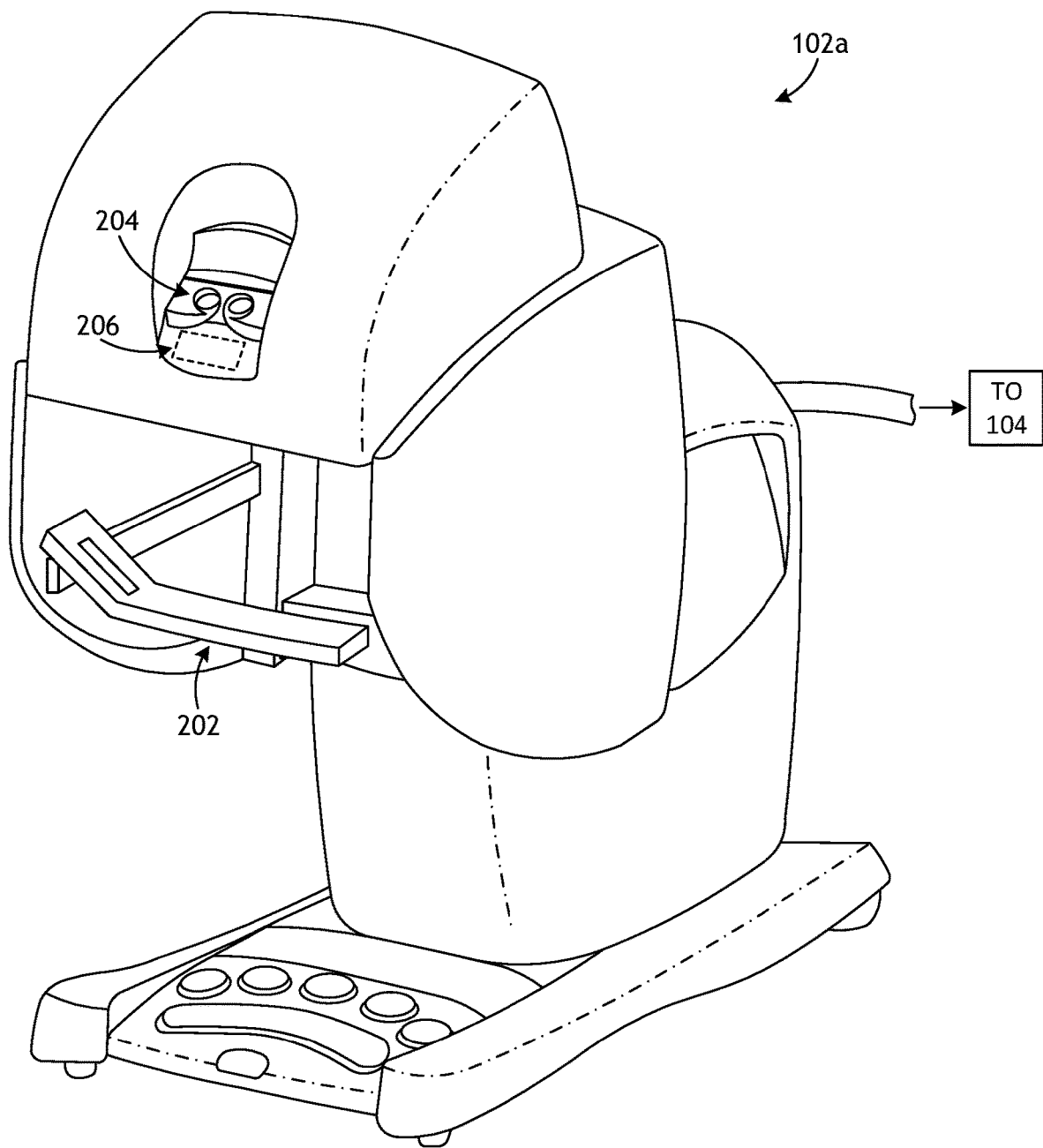
FIG. 2 is an example embodiment of the master controller of FIG. 1 that may be used to operate a robotic arm slave cart.

FIG. 2 is an example embodiment of the master controller 102a that may be used to operate a robotic arm slave cart, such as the arm cart 104 of FIG. 1. The master controller 102a and its associated arm cart 104, as well as their respective components and control systems, are collectively referred to herein as a "robotic surgical system." Examples of such systems and devices are disclosed in U.S. Pat. No. 7,524,320 and, therefore, will not be described in detail herein beyond that which may be necessary to understand various embodiments and forms of the present invention.

The master controller 102a generally includes one or more controllers 202 that can be grasped by a surgeon (e.g., the clinician 112a of FIG. 1) and manipulated in space while the surgeon views the procedure via a stereo display 204. The master controllers 202 generally comprise manual input devices designed to move in multiple degrees of freedom, and which often further have an actuatable handle for actuating a surgical instrument (e.g., the surgical instrument(s) 108 of FIG. 1), for example, for opening and closing opposing jaws, applying an electrical potential to an electrode, or the like.

In the illustrated example, the master controller 102a further includes an optional feedback meter 206 viewable by the surgeon via the display 204 to provide the surgeon with a visual indication of the amount of force being applied to the surgical instrument (i.e., a cutting instrument or dynamic clamping member). Other sensor arrangements may be employed to provide the master controller 102a with an indication of other surgical instrument metrics, such as whether a staple cartridge has been loaded into an end effector or whether an anvil has been moved to a closed position prior to firing, for example.

Figure 3:
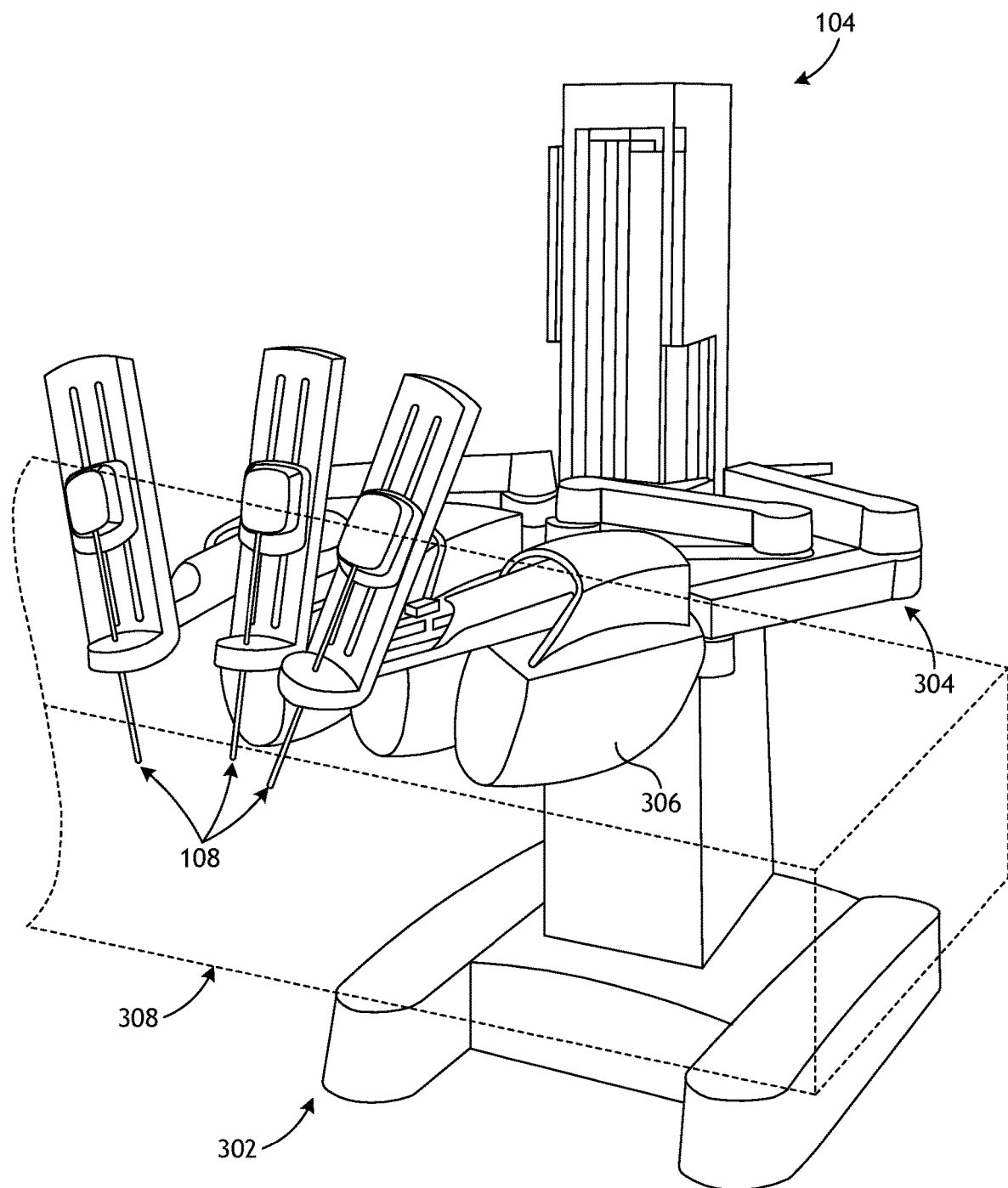
FIG. 3 depicts an example embodiment of the robotic arm cart of FIG. 1 used to actuate a plurality of surgical instruments.

FIG. 3 depicts an example embodiment of the robotic arm cart 104 used to actuate a plurality of surgical instruments 108, alternately referred to as "surgical tools." Various robotic surgery systems and methods employing master controller and robotic arm cart arrangements are described in U.S. Pat. No. 6,132,368, the contents of which are hereby incorporated by reference. As illustrated, the robotic arm cart 104 may include a base 302 that supports three surgical instruments 108, and the surgical instruments 108 are each supported by a series of manually articulatable linkages, generally referred to as set-up joints 304, and a robotic manipulator 306. These structures are herein illustrated with protective covers extending over much of the robotic linkage. These protective covers may be optional, and may be limited in size or entirely eliminated in some embodiments to minimize the inertia that is encountered by the servo mechanisms used to manipulate such devices, to limit the volume of moving components so as to avoid collisions, and to limit the overall weight of the cart 104.

The cart 104 will generally have dimensions suitable for transporting the cart 104 between operating rooms. The cart 104 may be configured to typically fit through standard operating room doors and onto standard hospital elevators. In some embodiments, the cart 104 may include a wheeled system (or other transportation system) that allows the cart 104 to be positioned adjacent an operating table by a single attendant. In various embodiments, an automated reloading system including a base portion may be strategically located within a work envelope 308 of the robotic arm cart 104.

Figure 4:
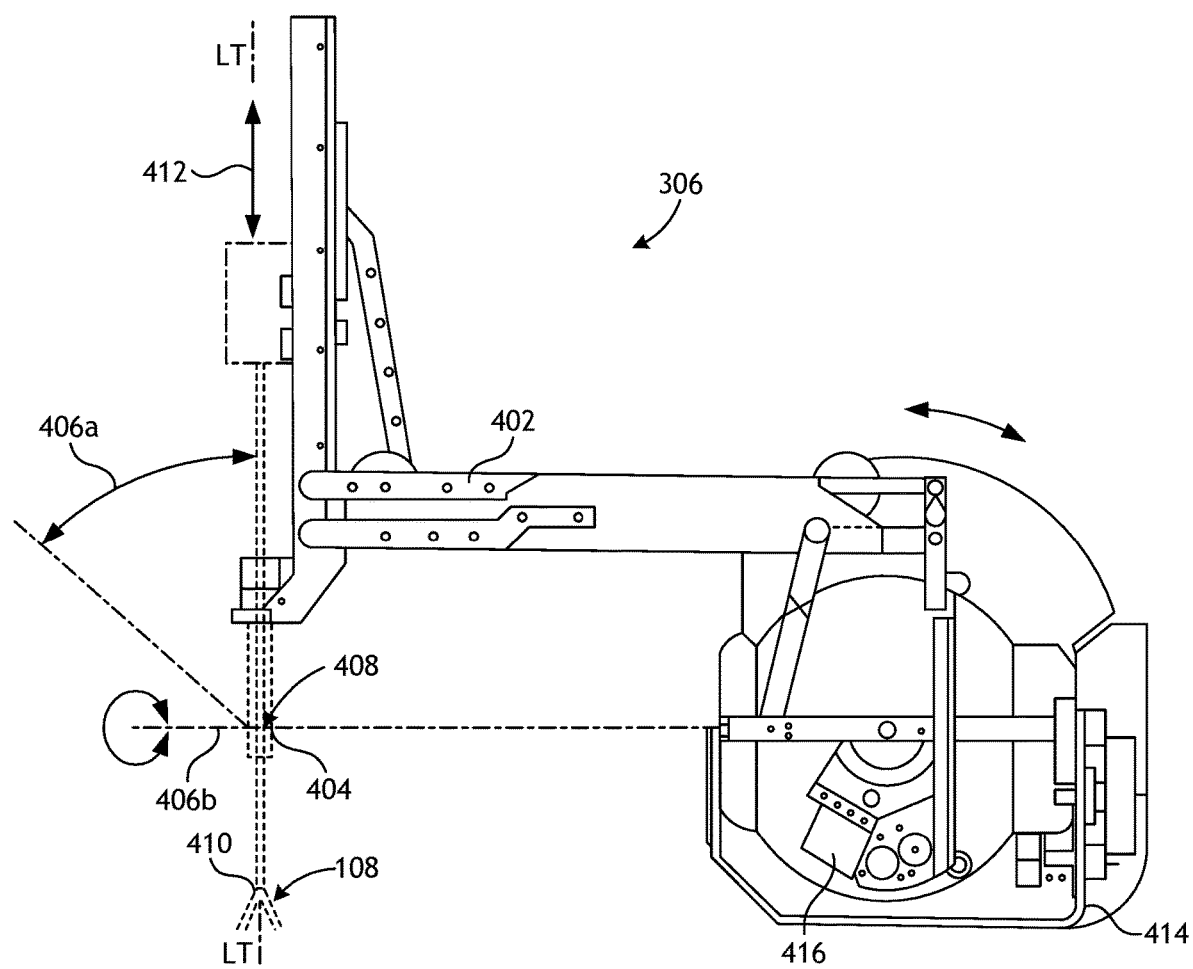
FIG. 4 is a side view schematic diagram of an example embodiment of the robotic manipulator of FIG. 3.

FIG. 4 is a side view schematic diagram of an example embodiment of the robotic manipulator 306. As illustrated, the robotic manipulator 306 may include linkage 402 that constrains movement of the surgical instrument 108 coupled thereto. The linkage 402 includes rigid links coupled by rotational joints in a parallelogram arrangement so that the surgical instrument 108 rotates around a point 404 in space.

The parallelogram arrangement constrains rotation to pivoting about a "pitch axis" that extends axis through the point 404, as indicated by a pitch arrow 406a. The links supporting the parallelogram linkage 402 are pivotally mounted to set-up joints 304 (FIG. 3) so that the surgical instrument 108 further rotates about a second axis 406b, referred to as the "yaw axis." The pitch axis and the yaw axis 406b intersect at a remote center 408, which is aligned along a shaft 410 of the surgical instrument 108.

The surgical instrument 108 may have further degrees of driven freedom as supported by the robotic manipulator 306, including sliding motion of the surgical instrument 108 along a longitudinal tool axis "LT-LT". As the surgical instrument 108 slides (translates) along the longitudinal tool axis LT-LT relative to the robotic manipulator 306 (arrow 412), the remote center 408 remains fixed relative to a base 414 of the robotic manipulator 306. Hence, the entire robotic manipulator 306 is generally moved to re-position the remote center 408.

The linkage 402 of the robotic manipulator 306 is driven by a series of motors 416. These motors 416 actively move the linkage 402 in response to commands from a processor of a control system. The motors 416 may also be employed to manipulate the surgical instrument 108.

Figure 5:
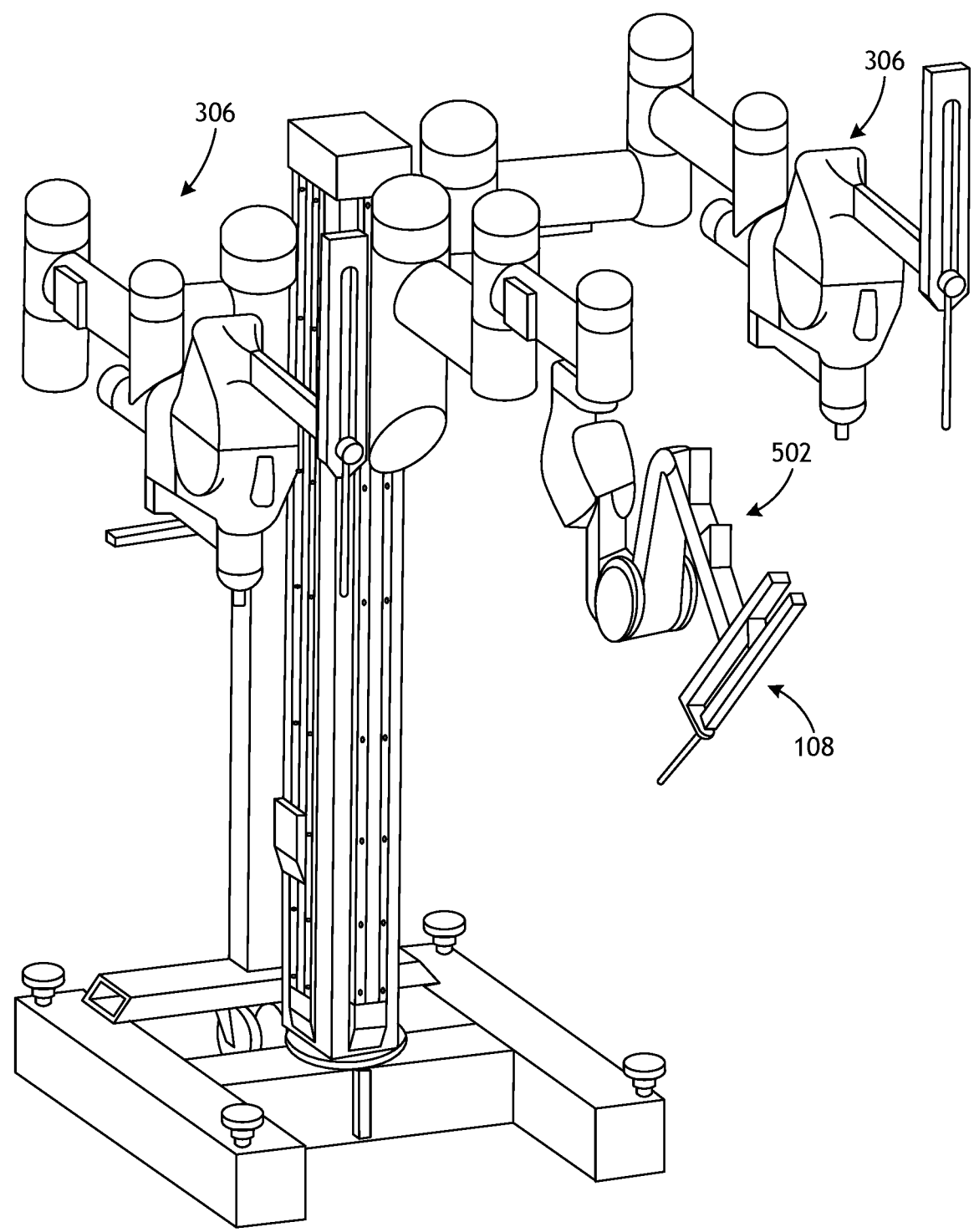
FIG. 5 is a perspective view of an alternative example robotic manipulator.

FIG. 5 is a perspective view of an alternative example robotic manipulator 502, used in conjunction with two robotic manipulators similar to the robotic manipulators 306 described in FIG. 4. As illustrated, a surgical instrument 108 is supported by the robotic manipulator 502 between the two robotic manipulators 306 generally described above. Those of ordinary skill in the art will appreciate that various embodiments of the present invention may incorporate a wide variety of alternative robotic structures, including those described in U.S. Pat. No. 5,878,193, the contents of which are hereby incorporated by reference. Additionally, while the data communication between a robotic component and the processor of the robotic surgical system is primarily described herein with reference to communication between the surgical instrument 108 and the master controller 102a (FIG. 2), it should be understood that similar communication may take place between circuitry of a robotic manipulator, a set-up joint, an endoscope or other image capture device, or the like, and the processor of the robotic surgical system for component compatibility verification, component-type identification, component calibration (such as off-set or the like) communication, confirmation of coupling of the component to the robotic surgical system, or the like.

Figure 6:
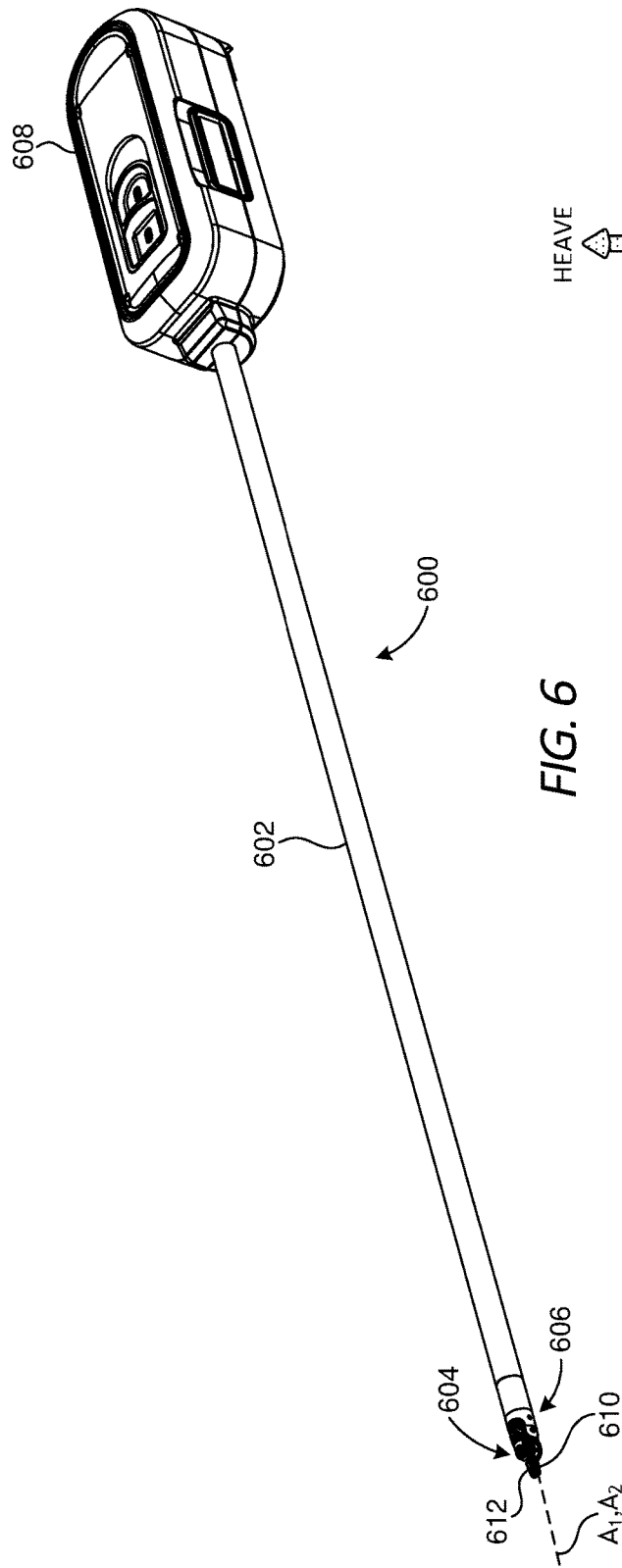
FIG. 6 is a side view of an example surgical tool that may incorporate some or all of the principles of the present disclosure.

FIG. 6 is side view of an example surgical tool 600 that may incorporate some or all of the principles of the present disclosure. The surgical tool 600 may be the same as or similar to the surgical instrument(s) 108 of FIGS. 1 and 3-5) and, therefore, may be used in conjunction with a robotic surgical system, such as the robotic surgical system 100 of FIG. 1. Accordingly, the surgical tool 600 may be designed to be releasably coupled to a tool driver included in the robotic surgical system 100.

As illustrated, the surgical tool 600 includes an elongate shaft 602, an end effector 604, a wrist 606 (alternately referred to as a "wrist joint") that couples the end effector 604 to the distal end of the shaft 602, and a drive housing 608 coupled to the proximal end of the shaft 602. In applications where the surgical tool is used in conjunction with a robotic surgical system (e.g., the robotic surgical system 100 of FIG. 1), the drive housing 608 can include coupling features that releasably couple the surgical tool 600 to the robotic surgical system. It will be appreciated, however, that the principles of the present disclosure are equally applicable to surgical tools that are non-robotic and otherwise manually manipulated.

The terms "proximal" and "distal" are defined herein relative to a robotic surgical system having an interface configured to mechanically and electrically couple the surgical tool 600 (e.g., the housing 608) to a robotic manipulator. The term "proximal" refers to the position of an element closer to the robotic manipulator and the term "distal" refers to the position of an element closer to the end effector 604 and thus further away from the robotic manipulator. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

During use of the surgical tool 600, the end effector 604 is configured to move (pivot) relative to the shaft 602 at the wrist 606 to position the end effector 604 at desired orientations and locations relative to a surgical site. The housing 608 includes (contains) various mechanisms designed to control operation of various features associated with the end effector 604 (e.g., clamping, firing, rotation, articulation, energy delivery, etc.). In at least some embodiments, the shaft 602 (and hence the end effector 604 coupled thereto) is configured to rotate about a longitudinal axis $A_1$ of the shaft 602. In such embodiments, at least one of the mechanisms included (housed) in the housing 608 is configured to control rotational movement of the shaft 602 about the longitudinal axis $A_1$.

The surgical tool 600 can have any of a variety of configurations capable of performing at least one surgical function. For example, the surgical tool 600 may include, but is not limited to, forceps, a grasper, a needle driver, scissors, an electro cautery tool, a stapler, a clip applier, a suction tool, an irrigation tool, an imaging device (e.g., an endoscope or ultrasonic probe), or any combination thereof. In some embodiments, the surgical tool 600 may be configured to apply energy to tissue, such as radiofrequency (RF) energy.

The shaft 602 is an elongate member extending distally from the housing 608 and has at least one lumen extending therethrough along its axial length. In some embodiments, the shaft 602 may be fixed to the housing 608, but could alternatively be rotatably mounted to the housing 608 to allow the shaft 602 to rotate about the longitudinal axis $A_1$. In yet other embodiments, the shaft 602 may be releasably coupled to the housing 608, which may allow a single housing 608 to be adaptable to various shafts having different end effectors.

The end effector 604 can have a variety of sizes, shapes, and configurations. In the illustrated embodiment, the end effector 604 includes opposing jaws 610, 612 configured to move (articulate) between open and closed positions. Accordingly, the end effector 604 can comprise, but is not limited to, a tissue grasper, a clip applier, scissors, a needle driver, a babcock including a pair of opposed grasping jaws, etc. One or both of the jaws 610, 612 may be configured to pivot at the wrist 606 to articulate the end effector 604 between the open and closed positions.

Figure 7:
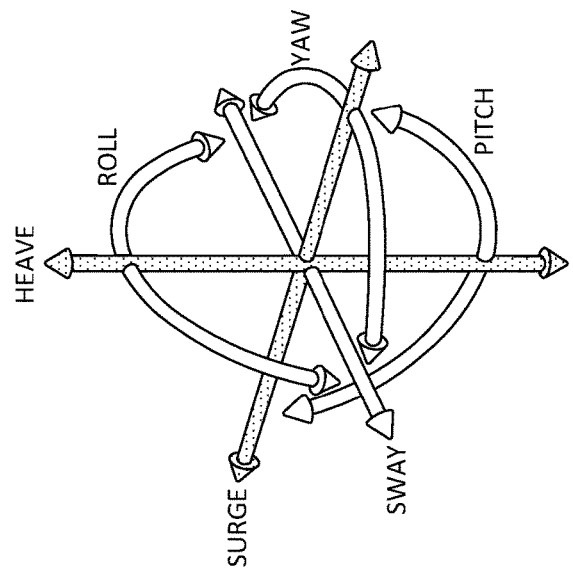
FIG. 7 illustrates potential degrees of freedom in which the wrist of FIG. 6 may be able to articulate (pivot).

FIG. 7 illustrates the potential degrees of freedom in which the wrist 606 may be able to articulate (pivot). The wrist 606 can have any of a variety of configurations. In general, the wrist 606 comprises a joint configured to allow pivoting movement of the end effector 604 relative to the shaft 602. The degrees of freedom of the wrist 606 are represented by three translational variables (i.e., surge, heave, and sway), and by three rotational variables (i.e., Euler angles or roll, pitch, and yaw). The translational and rotational variables describe the position and orientation of a component of a surgical system (e.g., the end effector 604) with respect to a given reference Cartesian frame. As depicted in FIG. 7, "surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

The pivoting motion can include pitch movement about a first axis of the wrist 606 (e.g., X-axis), yaw movement about a second axis of the wrist 606 (e.g., Y-axis), and combinations thereof to allow for 360° rotational movement of the end effector 604 about the wrist 606. In other applications, the pivoting motion can be limited to movement in a single plane, e.g., only pitch movement about the first axis of the wrist 606 or only yaw movement about the second axis of the wrist 606, such that the end effector 604 moves only in a single plane.

Referring again to FIG. 6, the surgical tool 600 includes a plurality of drive cables (obscured in FIG. 6) that form part of a cable driven motion system configured to facilitate movement of (articulate) the end effector 604 relative to the shaft 602. Moving the drive cables moves the end effector 604 between an unarticulated position and an articulated position. The end effector 604 is depicted in FIG. 6 in the unarticulated position where a longitudinal axis $A_2$ of the end effector 604 is substantially aligned with the longitudinal axis $A_1$ of the shaft 602, such that the end effector 604 is at a substantially zero angle relative to the shaft 602. Due to factors such as manufacturing tolerance and precision of measurement devices, the end effector 604 may not be at a precise zero angle relative to the shaft 602 in the unarticulated position, but nevertheless be considered "substantially aligned" thereto. In the articulated position, the longitudinal axes $A_1$, $A_2$ would be angularly offset from each other such that the end effector 604 is at a non-zero angle relative to the shaft 602.

Figure 8:
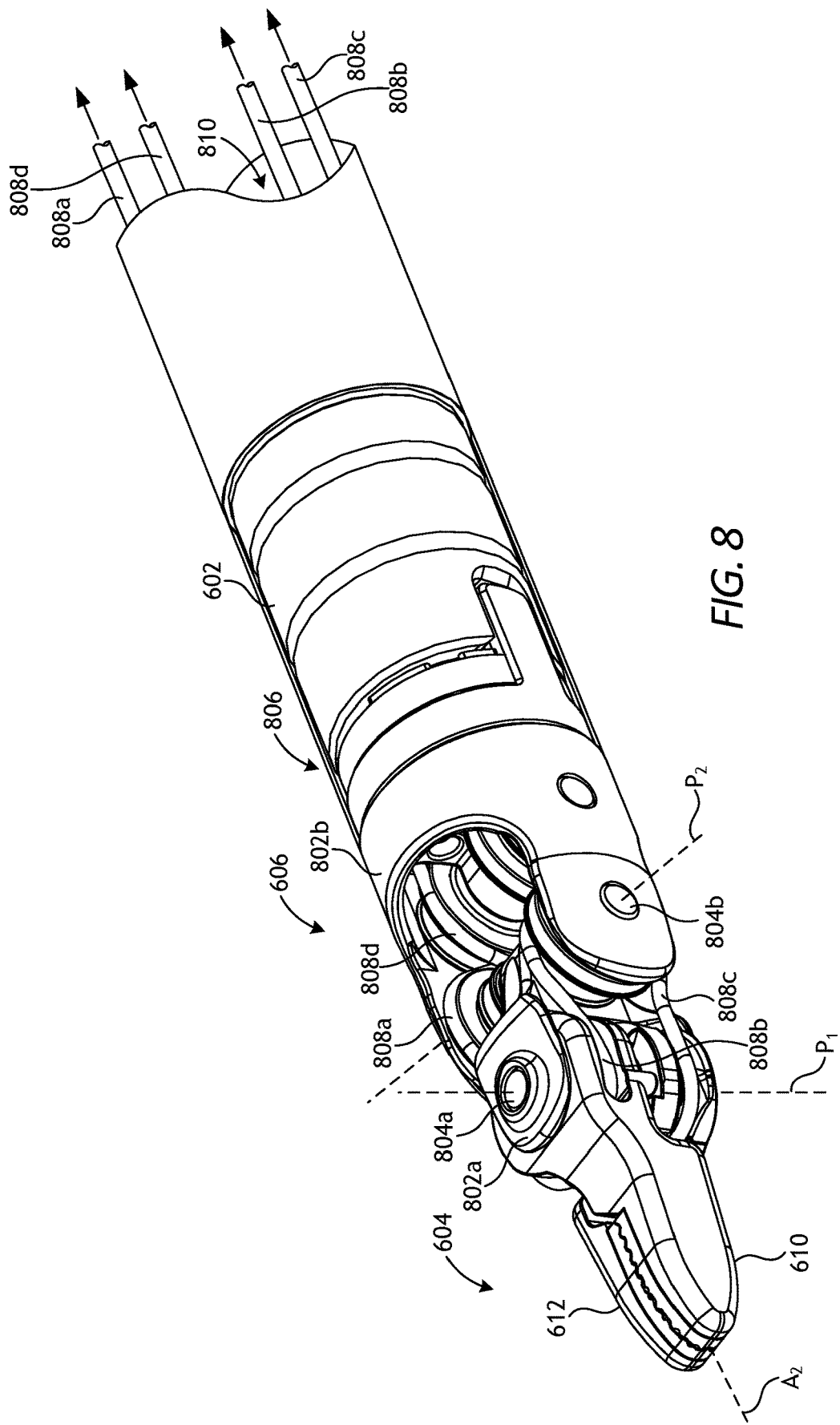
FIG. 8 is an enlarged isometric view of the distal end of the surgical tool of FIG. 6.

FIG. 8 is an enlarged isometric view of the distal end of the surgical tool 600 of FIG. 6. More specifically, FIG. 8 depicts enlarged views of the end effector 604 and the wrist 606, with the end effector 604 in the unarticulated position where the jaws 610, 612 are closed. The wrist 606 operatively couples the end effector 604 to the shaft 602. To accomplish this, the wrist 606 includes a distal clevis 802a and a proximal clevis 802b. The end effector 604 (i.e., the jaws 610, 612) is rotatably mounted to the distal clevis 802a at a first axle 804a, the distal clevis 802a is rotatably mounted to the proximal clevis 802b at a second axle 804b, and the proximal clevis 802b is coupled to a distal end 806 of the shaft 602.

The wrist 606 provides a first pivot axis $P_1$ that extends through the first axle 804a and a second pivot axis $P_2$ that extends through the second axle 804b. The first pivot axis $P_1$ is substantially perpendicular (orthogonal) to the longitudinal axis $A_2$ of the end effector 604, and the second pivot axis $P_2$ is substantially perpendicular (orthogonal) to both the longitudinal axis $A_2$ and the first pivot axis $P_1$. Movement about the first pivot axis $P_1$ provides "yaw" articulation of the end effector 604, and movement about the second pivot axis $P_2$ provides "pitch" articulation of the end effector 604. In the illustrated embodiment, the jaws 610, 612 are mounted at the first pivot axis $P_1$, thereby allowing the jaws 610, 612 to pivot relative to each other to open and close the end effector 604 or alternatively pivot in tandem to articulate the orientation of the end effector 604.

A plurality of drive cables, shown as drive cables 808a, 808b, 808c, and 808d, extend longitudinally within a lumen 810 defined by the shaft 602 and pass through the wrist 606 to be operatively coupled to the end effector 604. The drive cables 808a-d form part of the cable driven motion system briefly described above, and may be referred to and otherwise characterized as cables, bands, lines, cords, wires, ropes, strings, twisted strings, elongate members, etc. The drive cables 808a-d can be made from a variety of materials including, but not limited to, metal (e.g., tungsten, stainless steel, etc.) or a polymer. Example drive cables are described in U.S. Patent Pub. No. 2015/0209965 entitled "Compact Robotic Wrist," and U.S. Patent Pub. No. 2015/0025549 entitled "Hyperdexterous Surgical System," the contents of which are hereby incorporated by reference. The lumen 810 can be a single lumen, as illustrated, or can alternatively comprise a plurality of independent lumens that each receive one or more of the drive cables 808a-d.

The drive cables 808a-d extend proximally from the end effector 604 to the drive housing 608 (FIG. 6) where they are operatively coupled to various actuation mechanisms or devices housed (contained) therein to facilitate longitudinal movement (translation) of the drive cables 808a-d within the lumen 810. Selective actuation of all or a portion of the drive cables 808a-d causes the end effector 604 (e.g., one or both of the jaws 610, 612) to articulate (pivot) relative to the shaft 602. More specifically, selective actuation causes a corresponding drive cable 808a-d to translate longitudinally within the lumen 810 and thereby cause pivoting movement of the end effector 604. One or more drive cables 808a-d, for example, may translate longitudinally to cause the end effector 604 to articulate (e.g., both of the jaws 610, 612 angled in a same direction), to cause the end effector 604 to open (e.g., one or both of the jaws 610, 612 move away from the other), or to cause the end effector 604 to close (e.g., one or both of the jaws 610, 612 move toward the other).

Moving the drive cables 808a-d can be accomplished in a variety of ways, such as by triggering an associated actuator or mechanism operatively coupled to or housed within the drive housing 608 (FIG. 6). Moving a given drive cable 808a-d constitutes applying tension (i.e., pull force) to the given drive cable 808a-d in a proximal direction, which causes the given drive cable 808a-d to translate and thereby cause the end effector 604 to move (articulate) relative to the shaft 602.

The wrist 606 includes a first plurality of pulleys 812a and a second plurality of pulleys 812b, each configured to interact with and redirect the drive cables 808a-d for engagement with the end effector 604. The first plurality of pulleys 812a is mounted to the proximal clevis 802b at the second axle 804b and the second plurality of pulleys 812b is also mounted to the proximal clevis 802b but at a third axle 804c located proximal to the second axle 804b. The first and second pluralities of pulleys 812a,b cooperatively redirect the drive cables 808a-d through an "S" shaped pathway before the drive cables 808a-d are operatively coupled to the end effector 604.

In at least one embodiment, one pair of drive cables 808a-d is operatively coupled to each jaw 610, 612 and configured to "antagonistically" operate the corresponding jaw 610, 612. In the illustrated embodiment, for example, the first and second drive cables 808a,b may be coupled at the first jaw 610, and the third and fourth drive cables 808c,d may be coupled at the second jaw 612. Actuation of the first drive cable 808a acts on and pivots the first jaw 610 about the first pivot axis $P_1$ toward the open position. In contrast, actuation of the second drive cable 808b also acts on and pivots the first jaw 610 about the first pivot axis $P_1$ in the opposite direction and toward the closed position. Similarly, actuation of the third drive cable 808c acts and pivots the second jaw 612 about the first pivot axis $P_1$ toward the open position, while actuation of the fourth drive cable 808d also acts on but pivots the second jaw 612 about the first pivot axis $P_1$ in the opposite direction and toward the closed position.

Accordingly, the drive cables 808a-d may be characterized or otherwise referred to as "antagonistic" cables that cooperatively (yet antagonistically) operate to cause relative or tandem movement of the first and second jaws 610, 612. When the first drive cable 808a is actuated (moved), the second drive cable 808b naturally follows as coupled to the first drive cable 808a, and vice versa. Similarly, when the third drive cable 808c is actuated, the fourth drive cable 808d naturally follows as coupled to the third drive cable 808c, and vice versa.

Moreover, coordinated actuation of the drive cables 808a-d may also articulate the end effector 604 about the second pivot axis $P_2$. Consequently, the end effector 604 can articulate with multiple degrees of freedom, e.g., a degree of freedom by articulating about the first pivot axis $P_1$ and another degree of freedom by articulating about the second pivot axis $P_2$. The wrist 606 in this embodiment is pivotable about the second pivot axis $P_2$ in a single plane, e.g., in one of pitch and yaw, and the end effector 604 is pivotable about the first pivot axis $P_1$ in a single, different plane, e.g., the other of pitch and yaw.

Figure 9:
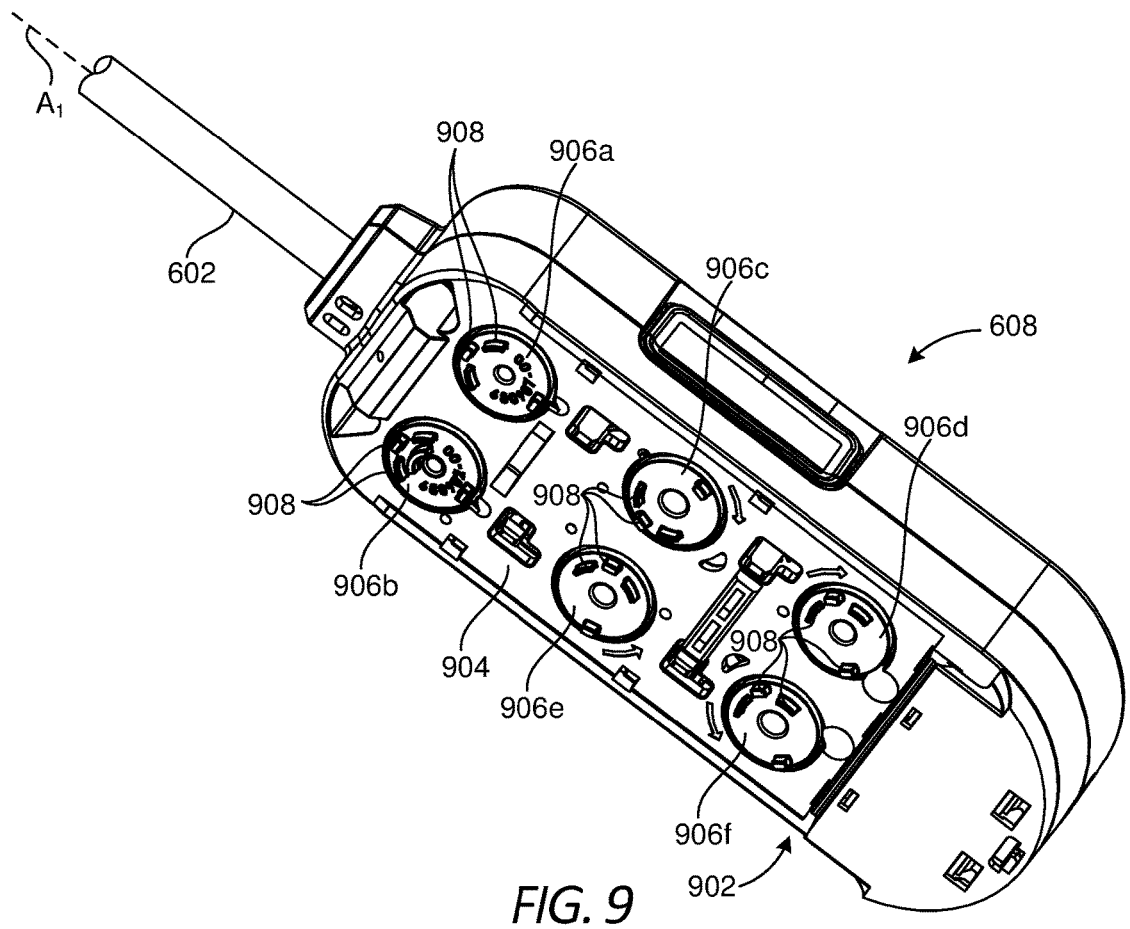
FIG. 9 is a bottom view of the drive housing of the surgical tool of FIG. 6.

FIG. 9 is a bottom view of the drive housing 608, according to one or more embodiments. As illustrated, the drive housing 608 (alternately referred to as a "puck") may include a tool mounting portion 902 used to operatively couple the drive housing 608 to a tool driver of a robotic manipulator (e.g., the robotic manipulators 306, 502 of FIGS. 3 and 5, respectively). The tool mounting portion 902 may releasably couple the drive housing 608 to a tool driver in a variety of ways, such as by clamping thereto, clipping thereto, or slidably mating therewith. In some embodiments, the tool mounting portion 902 may include an array of electrical connecting pins, which may be coupled to an electrical connection on the mounting surface of the tool driver. While the tool mounting portion 902 is described herein with reference to mechanical, electrical, and magnetic coupling elements, it should be understood that a wide variety of telemetry modalities might be used, including infrared, inductive coupling, or the like.

The tool mounting portion 902 includes and otherwise provides an interface 904 configured to mechanically, magnetically, and/or electrically couple the drive housing 608 to the tool driver. As illustrated, the interface 904 includes and supports a plurality of inputs, shown as drive inputs 906a, 906b, 906c, 906d, 906e, and 906f. In at least one embodiment, each drive input 906a-f comprises a rotatable disc configured to align with and couple to a corresponding actuator of a given tool driver. Moreover, each drive input 906a-f provides or defines one or more surface features 908 configured to align with mating surface features provided on the corresponding actuator. The surface features 908 can include, for example, various protrusions and/or indentations that facilitate a mating engagement. In some embodiments, some or all of the drive inputs 906a-f may include one surface feature 908 that is positioned closer to an axis of rotation of the associated drive input 906a-f than the other surface feature(s) 908. This may help to ensure positive angular alignment of each drive input 906a-f.

In some embodiments, actuation of the first drive input 906a may be configured to control rotation of the elongate shaft 602 about its longitudinal axis $A_1$. The elongate shaft 602 may be rotated clockwise or counter-clockwise depending on the rotational actuation of the first drive input 906a. In some embodiments, actuation of the second drive input 906b may be configured to control a lockout mechanism (alternately referred to as a deadbolt), which locks the end effector 604 (FIGS. 6 and 8) in a predetermined pose or position. In some embodiments, actuation of the third, fourth, fifth, and sixth drive inputs 906c-f may be configured to operate movement (axial translation) of the drive cables 808a-d (FIG. 8), respectively, which results in the articulation of the end effector 604. Each of the drive inputs 906a-f may be actuated based on user inputs communicated to a tool driver coupled to the interface 904, and the user inputs may be received via a computer system incorporated into the robotic surgical system.

Figure 10:
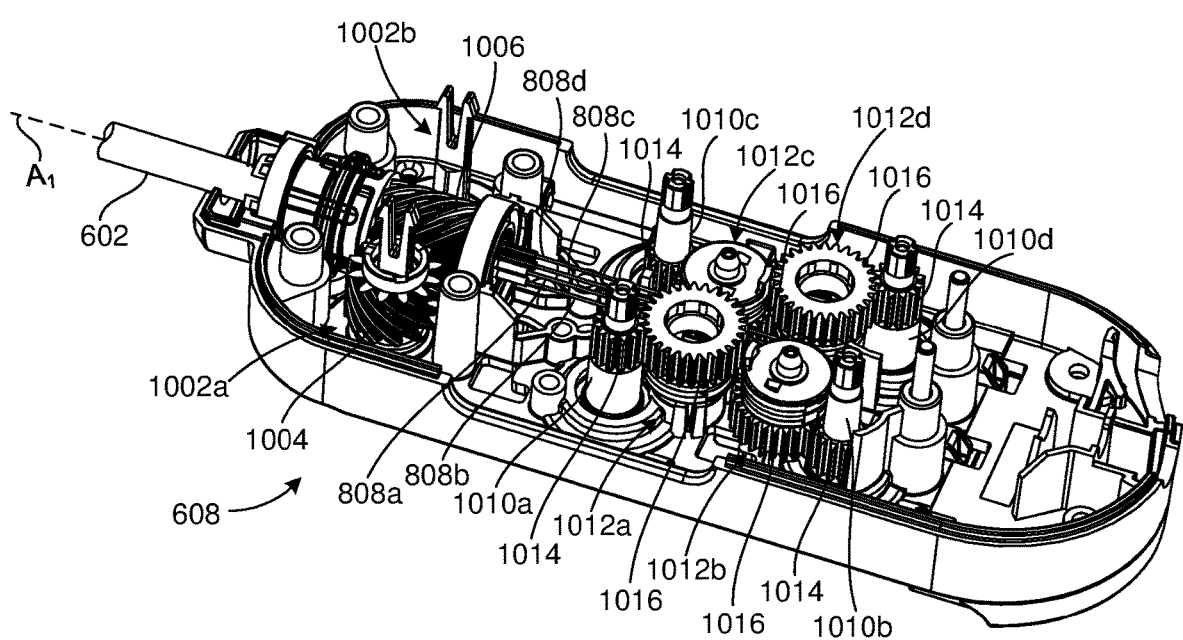
FIG. 10 is an isometric exposed view of the interior of the drive housing of the surgical tool of FIG. 6.

FIG. 10 is an isometric exposed view of the interior of the drive housing 608, according to one or more embodiments. Several component parts that may be otherwise contained within the drive housing 608 are not shown in FIG. 10 to enable discussion of the depicted component parts. As illustrated, a first capstan 1002a and a second capstan 1002b (only partially visible) are contained (housed) within the drive housing 608. The first capstan 1002a may be operatively coupled to or extend from the first drive input 906a (FIG. 9), and the second capstan 1002b may be operatively coupled to or extend from the second drive input 906b (FIG. 9). Accordingly, actuation of the first drive input 906a results in rotation of the first capstan 1002a and actuation of the second drive input 906b results in rotation of the second capstan 1002b.

A spiral worm drive gear 1004 is coupled to or forms part of the first capstan 1002a. The spiral worm drive gear 1004 may be configured to mesh and interact with a driven gear 1006 secured within the drive housing 608 and operatively coupled to the shaft 602 such that rotation of the driven gear 1006 correspondingly rotates the shaft 602. Accordingly, rotation of the spiral worm drive gear 1004 (via actuation of the first drive input 906a of FIG. 9) will drive the driven gear 1006 and thereby control rotation of the elongate shaft 602 about the longitudinal axis $A_1$.

In some embodiments, the second capstan 1002b may have a pinion gear (not shown) coupled thereto and configured to mesh and interact with a rack (not shown) contained within the drive housing 608. The rack may be operatively coupled to a lockout mechanism that is movable to lock the end effector 604 (FIGS. 6 and 8) in a predetermined pose or position. Accordingly, rotation of the pinion gear (via actuation of the second drive input 906b of FIG. 9) will control the lockout mechanism and thereby lock and unlock the end effector 604 when desired.

The drive housing 608 further contains or houses a first input shaft 1010a, a second input shaft 1010b, a third input shaft 1010c, and a fourth input shaft 1010d. In the illustrated embodiment, the first input shaft 1010a is operatively coupled to or extends from the third drive input 906c (FIG. 9), the second input shaft 1010b is operatively coupled to or extends from the fourth drive input 906d (FIG. 9), the third input shaft 1010c is operatively coupled to or extends from the fifth drive input 906e (FIG. 9), and the fourth input shaft 1010d is operatively coupled to or extends from the sixth drive input 906f (FIG. 9). Accordingly, actuation of the third drive input 906c results in rotation of the first input shaft 1010a, actuation of the fourth drive input 906d results in rotation of the second input shaft 1010b, actuation of the fifth drive input 906e results in rotation of the third input shaft 1010c, and actuation of the sixth drive input 906f results in rotation of the fourth input shaft 1010d. While four input shafts 1010a-d are depicted in FIG. 10, it is contemplated herein to include more or less than four, without departing from the scope of the disclosure.

The drive housing 608 further contains or houses a first drive cable capstan 1012a, a second drive cable capstan 1012b, a third drive cable capstan 1012c, and a fourth drive cable capstan 1012d. Each drive cable capstan 1012a-d is rotatably mounted within the drive housing 608 and one of the drive cables 808a-d is operatively coupled to (e.g., wrapped only partially around) a corresponding on of the drive cable capstans 1012a-d. More specifically, the first drive cable 808a is coupled to the first drive cable capstan 1012a, the second drive cable 808b is coupled to the second drive cable capstan 1012b, the third drive cable 808c is coupled to the third drive cable capstan 1012c, and the fourth drive cable 808d is coupled to the fourth drive cable capstan 1012d.

As illustrated, each input shaft 1010a-d has a drive gear 1014 coupled thereto or forming part thereof, and each drive cable capstan 1012a-d has a driven gear 1016 coupled thereto or forming part thereof. Each drive gear 1014 is positioned to mesh and interact with a corresponding driven gear 1016. In some embodiments, the drive and driven gears 1014, 1016 may comprise mating spur gears. Accordingly, rotation of the first input shaft 1010a (via actuation of the third drive input 906c of FIG. 9) will correspondingly rotate the associated drive gear 1014 and drive the associated driven gear 1016 to control movement of the first drive cable 808a; rotation of the second input shaft 1010b (via actuation of the fourth drive input 906d of FIG. 9) will correspondingly rotate the associated drive gear 1014 and drive the associated driven gear 1016 to control movement of the second drive cable 808b; rotation of the third input shaft 1010c (via actuation of the fifth drive input 906e of FIG. 9)

will correspondingly rotate the associated drive gear 1014 and drive the associated driven gear 1016 to control movement of the third drive cable 808*c*; and rotation of the fourth input shaft 1010*d* (via actuation of the sixth drive input 906*f* of FIG. 9) will correspondingly rotate the associated drive gear 1014 and drive the associated driven gear 1016 to control movement of the fourth drive cable 808*d*.

Figure 11:
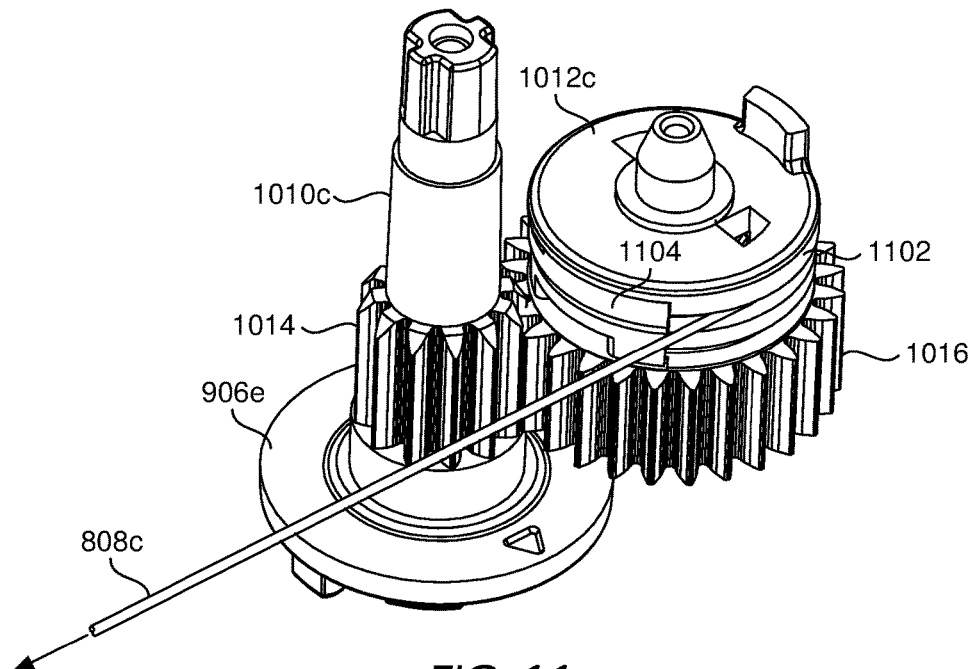
FIG. 11 is an isometric view of the third input shaft and the third drive cable capstan of FIG. 10.

FIG. 11 is an isometric view of the third input shaft 1010*c* and the third drive cable capstan 1012*c* cooperatively arranged for operation, according to one or more embodiments. The following description provides specifics and details of the third input shaft 1010*c* and the third drive cable capstan 1012*c*, but is equally applicable to any of the input shafts 1010*a-d* and drive cable capstans 1012*a-d* described herein with reference to FIG. 10. Accordingly, specifics and operation of the third input shaft 1010*c* and the third drive cable capstan 1012*c* may be equally applied to operation of the first input shaft 1010*a* and the first drive cable capstan 1012*a*, the second input shaft 1010*b* and the second drive cable capstan 1012*b*, and the fourth input shaft 1010*d* and the fourth drive cable capstan 1012*b*. More specifically, however, discussion of the third drive cable capstan 1012*c* (and its component parts) is equally applicable to the first, second, and fourth drive cable capstans 1012*a,b,d*.

As mentioned above, the third input shaft 1010*c* is operatively coupled to or extends from the fifth drive input 906*e* such that actuation of the fifth drive input 906*e* correspondingly rotates the third input shaft 1010*c* and its associated drive gear 1014. Moreover, as also mentioned above, the third drive cable 808*c* is coupled to (e.g., wraps around partially) the third drive cable capstan 1012*c*, which includes a driven gear 1016 configured to mesh and interact with the drive gear 1014 of the third input shaft 1010*c*. In example operation, actuating the fifth drive input 906*e* rotates the third input shaft 1010*c*, which correspondingly rotates the third drive cable capstan 1012*c* to control longitudinal movement of the third drive cable 808*c*.

As illustrated, the third drive cable 808*c* is received within a channel or pulley track 1102 defined on the third drive cable capstan 1012. The third drive cable 808*c* extends (wraps) only partially around the circumference of the third drive cable capstan 1012*c* within the pulley track 1102. As described in more detail below, a cable clip 1104 may be configured to receive an end of the third drive cable 808*c* and secure the third drive cable 808*c* to the third drive cable capstan 1012*c*.

The third drive cable 808*c* wraps partially around the third drive cable capstan 1012*c* and is fed directly into the shaft 602 (FIGS. 6 and 10) from the pulley track 1102. Consequently, the third drive cable 808*c* interacts with only the third drive cable capstan 1012*c* during operation, which substantially mitigates cable derailment risks. In contrast, other surgical tools use the input shaft as the drive cable capstan in conjunction with an adjacent idler pulley that redirects the drive cable into the shaft for operation. As a result, the drive cable is required to wrap around both the input shaft (operating as the drive cable capstan) and the adjacent idler pulley, which presents two distinct tool locations that are susceptible to cable derailment. Wrapping the third drive cable 808*c* partially around only the third drive cable capstan 1012*c* limits cable derailment risks to only a single location, and feeding the third drive cable 808*c* directly into the shaft 602 from the third drive cable capstan 1012*c* eliminates the need for any idler pulleys. Moreover, not requiring an idler pulley reduces part count and weight in the system, and makes it easier to assemble.

The pulley track 1102 may be defined on the third drive cable capstan 1012*c* in a single plane. In other words, there are no vertical changes in the path length of the pulley track 1102 about the circumference of the third drive cable capstan 1012*c*. Consequently, the position of the third drive cable 808*c* does not change elevation as it extends (wraps) about the circumference of the third drive cable capstan 1012*c* within the pulley track 1102. In contrast, drive cables in other surgical tools are helically wrapped about the drive cable capstan (and/or an adjacent idler pulley) multiple times such that the position of the drive cable changes elevation as it extends about the circumference of the drive cable capstan (and/or the adjacent idler pulley). Wrapping the third drive cable 808*c* about the third drive cable capstan 1012*c* within the single plane pulley track 1102 eliminates minor changes in the overall path length of the third drive cable 808*c*, which also helps mitigate cable derailment risk. More specifically, the overall path length is reduced with a single plane embodiment, which means less of the third drive cable 808*c* would have to be re-railed within the pulley track 1102 if derailed during operation. Moreover, constraining the third drive cable 808*c* in a single plane helps the third drive cable 808*c* re-rail properly and more easily, as opposed to re-railing the third drive cable 808*c* if it were wrapped in a helical pattern multiple times about the third drive cable capstan 1012*c*.

By accepting a small power loss (e.g., in the form of increased friction) from the intermeshed drive and driven gears 1014, 1016, the single-wind and single-plane third drive cable capstan 1012*c* may prove advantageous in mitigating cable derailment risks. Moreover, the gear ratio between the drive and driven gears 1014, 1016 can be easily altered to allow for changing design criteria. In addition, the single-wind and single-plane characteristics of the third drive cable capstan 1012*c* allows the third drive cable capstan 1012*c* to be positioned relative to the shaft 602 (FIGS. 6 and 10) within the drive housing 608 (FIGS. 6 and 10). This provides the option of grouping the drive cable capstans 1012*a-d* closer together within the drive housing 608, and thereby freeing up space elsewhere.

Figure 12:
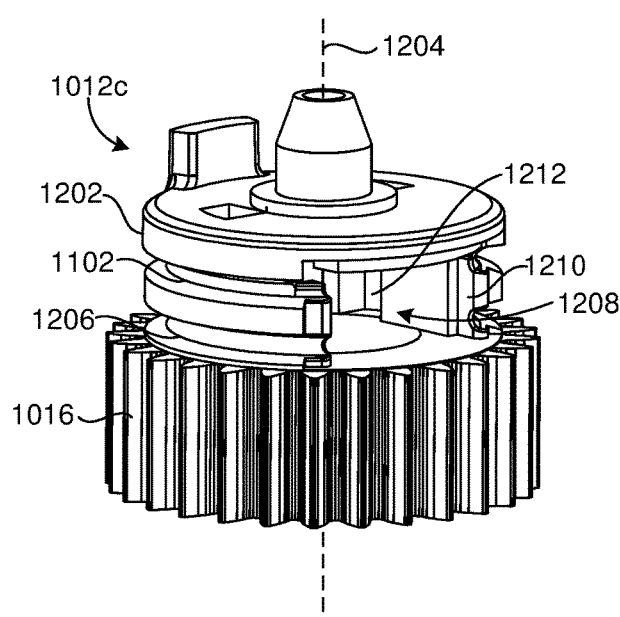
FIG. 12 is an isometric view of the third drive cable capstan of FIG. 11.

FIG. 12 is an isometric view of the third drive cable capstan 1012*c*, according to one or more embodiments. It is again noted that the accompanying description of the third drive cable capstan 1012*c* is equally applicable to the first, second, and/or fourth drive cable capstans 1012*a,b,d* of FIG. 10. Indeed, in at least one embodiment, each of the drive cable capstans 1012*a-d* may comprise an identical structure, but may be orientated differently within the drive housing 608 (FIG. 10). For example, the second and third drive cable capstans 1012*b,c* in FIG. 10 are oriented similarly within the drive housing 608, and the first and fourth drive cable capstans 1012*a,d* in FIG. 10 are oriented similarly within the drive housing 608 but flipped upside down as compared to the second and third drive cable capstans 1012*b,c*.

As illustrated, the third drive cable capstan 1012*c* comprises a generally cylindrical body 1202 having a longitudinal axis 1204 about which the body 1202 may rotate during operation. The driven gear 1016 is coupled to or forms an integral part of the outer radial surface of the body 1202. The driven gear 1016 extends about the entire circumference of the body 1202. The pulley track 1102 is also shown and is defined in the body 1202. In at least one embodiment, as illustrated, the body 1202 may provide and otherwise define a second pulley track 1206 axially offset from the first pulley track 1102. Similar to the first pulley track 1102, the second pulley track 1206 may be defined in a single plane one the third drive cable capstan 1012*c*. The second pulley track 1206 allows the third drive cable capstan 1012*c* to be used upside down, such as in the case of the first and fourth drive cable capstans 1012*a,d* of FIG. 10. In such applications, the corresponding drive cable may extend within the second pulley track 1206. As will be appreciated, this may prove advantageous in simplifying the manufacturing process and resulting in less unique parts to manufacture.

In some embodiments, as illustrated, the body 1202 may further provide and otherwise define a cavity 1208 configured to receive and secure the cable clip 1104 (FIGS. 11 and 13) to the third drive cable capstan 1012*c*. The cavity 1208 may provide an opening 1210 having a cross-sectional shape sized to receive a corresponding cross-sectional shape of the cable clip 1104. Moreover, the cavity 1208 may provide various internal features to help secure the cable clip 1104 within the cavity 1208. In at least one embodiment, for example, the cavity 1208 may define one or more recesses 1212 (one shown) configured to receive a corresponding protrusion or other protruding structure of the cable clip 1104.

In other embodiments, however, the cavity 1208 may be omitted from the body 1202 and the cable clip 1104 (FIGS. 11 and 13) may alternatively be secured to an outer surface of the body 1202 via a variety of other means. For example, the cable clip 1104 may be secured to an outer surface of the body 1202 using, but not limited to, one or more mechanical fasteners, an adhesive, a snap fit, an interference fit, welding, brazing, or any combination thereof. Accordingly, coupling the cable clip 1104 to the body 1202 can refer to receiving at least a portion of the cable clip 1104 within the cavity 1208, or otherwise securing the cable clip 1104 to an outer surface of the body 1202, without departing from the scope of the disclosure.

Figure 13:
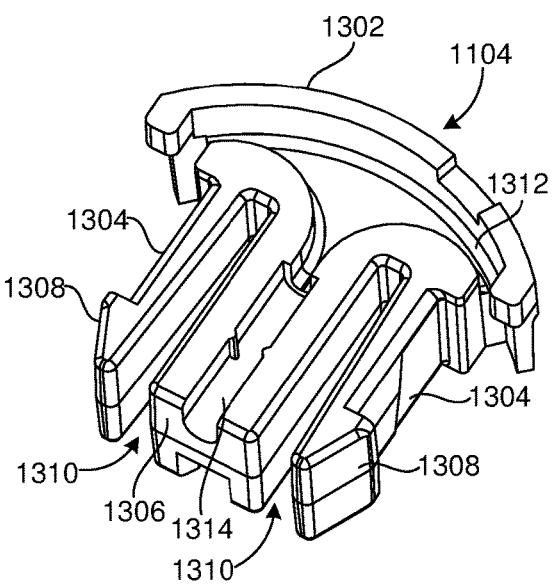
FIG. 13 is an isometric view of an example embodiment of the cable clip of FIG. 11, according

FIG. 13 is an isometric view of an example embodiment of the cable clip 1104, according to one or more embodiments. As illustrated, the cable clip 1104 includes a clip body 1302 that provides one or more longitudinally extending legs 1304 (two shown) and a center member 1306. In some embodiments, the longitudinally extending legs 1304 and the center member 1306 may be sized and otherwise configured to be received within the cavity 1208 (FIG. 12) of the third drive cable capstan 1012*c*. In at least one embodiment, a protrusion 1308 may be provided by or formed on one or both of the legs 1304. Each protrusion 1308 may be configured to be received within a corresponding one of the recesses 1212 (FIG. 12) defined within the cavity 1208 to provide a snap-fit engagement that secures the cable clip 1104 to the third drive cable capstan 1012*c*. A gap or space 1310 may be defined between the center member 1306, and each leg 1304 to allow the legs 1304 to flex inward upon entering the cavity 1208, and the leg(s) 1304 may flex back outward once the protrusion(s) 1308 locate the recess(es) 1212.

The clip body 1302 may further define a cable channel 1312 and a cable capture orifice 1314. The cable capture orifice 1314 communicates with the cable channel 1312 to enable receipt of an end of a drive cable (e.g., the third drive cable 808*c* of FIG. 11). More specifically, a drive cable can be received within the cable channel 1312 on either lateral side of the clip body 1302, and then routed into the cable capture orifice 1314 to secure the drive cable to the cable clip 1104.

In the illustrated embodiment, the cable capture orifice 1314 is defined on the central member 1306, but could alternatively be defined at any other location on the clip body 1302.

Figure 14:
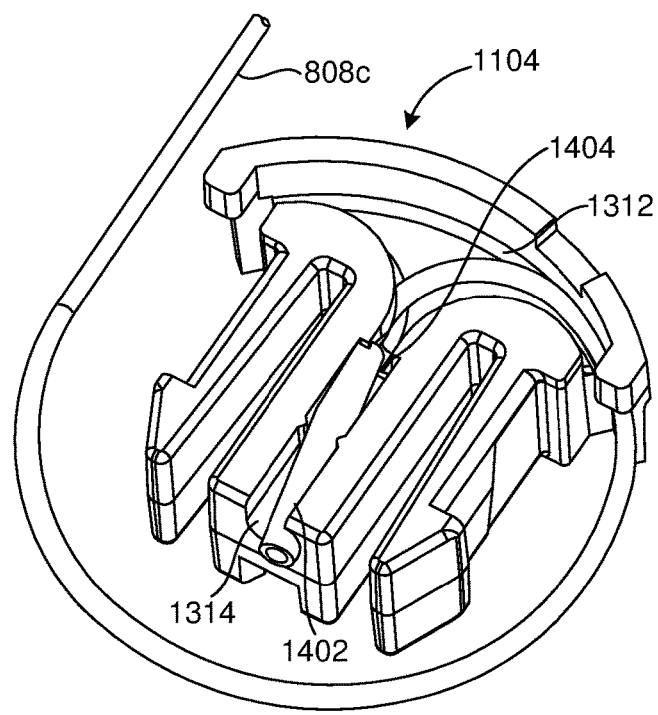
FIG. 14 is an isometric view of the cable clip of FIG. 13 having the third drive cable of FIG. 11 coupled thereto.

FIG. 14 is an isometric view of the cable clip 1104 having the third drive cable 808*c* coupled thereto, according to one or more embodiments. More specifically, as illustrated, the third drive cable 808*c* is received within the cable channel 1312 on one lateral side of the clip body 1302, and is then routed into the cable capture orifice 1314. In some embodiments, a connector 1402 may be provided at the end of the third drive cable 808*c* to secure the third drive cable 808*c* within the cable capture orifice 1314. The connector 1402 may comprise any connection device or means capable of securing the third drive cable 808*c* to the cable clip 1104. In the illustrated embodiment, for example, the connector 1402 comprises a crimp, such as a lead shot or the like, that is larger than an opening 1404 to the cable capture orifice 1314 to prevent the end of the third drive cable 808*c* from escaping the cable capture orifice 1314. Other suitable connectors 1402 may include, but are not limited to, a welded attachment, a brazed attachment, an adhesive bond, a mechanical fastener, or any combination thereof.

Figure 15:
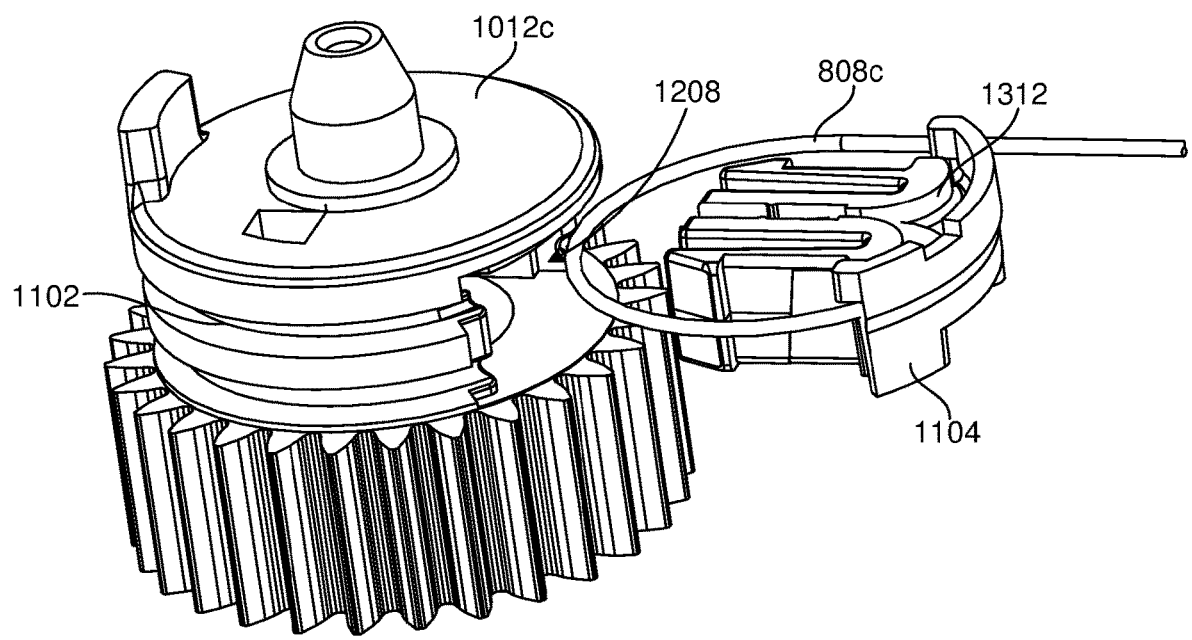
FIG. 15 is a partially exploded view of the third drive cable capstan and the cable clip of FIG. 11.

FIG. 15 is a partially exploded view of the third drive cable capstan 1012*c* and the cable clip 1104, according to one or more embodiments. As illustrated, the third drive cable 808*c* is coupled to the cable clip 1104, which is poised to be received within the cavity 1208. Before inserting the cable clip 1104 into the cavity 1208, the third drive cable 808*c* may be received within the pulley track 1102 and routed partially around the outer circumference of the third drive cable capstan 1012*c*. The cable clip 1104 may then be coupled to the third drive cable capstan 1012*c* in a snap-fit engagement, as generally described above. When the cable clip 1104 is coupled to the third drive cable capstan 1012*c*, the cable channel 1312 will align with the pulley track 1102 to allow the third drive cable 808*c* to transition easily from the pulley track 1102 to the cable channel 1312.

Figure 16:
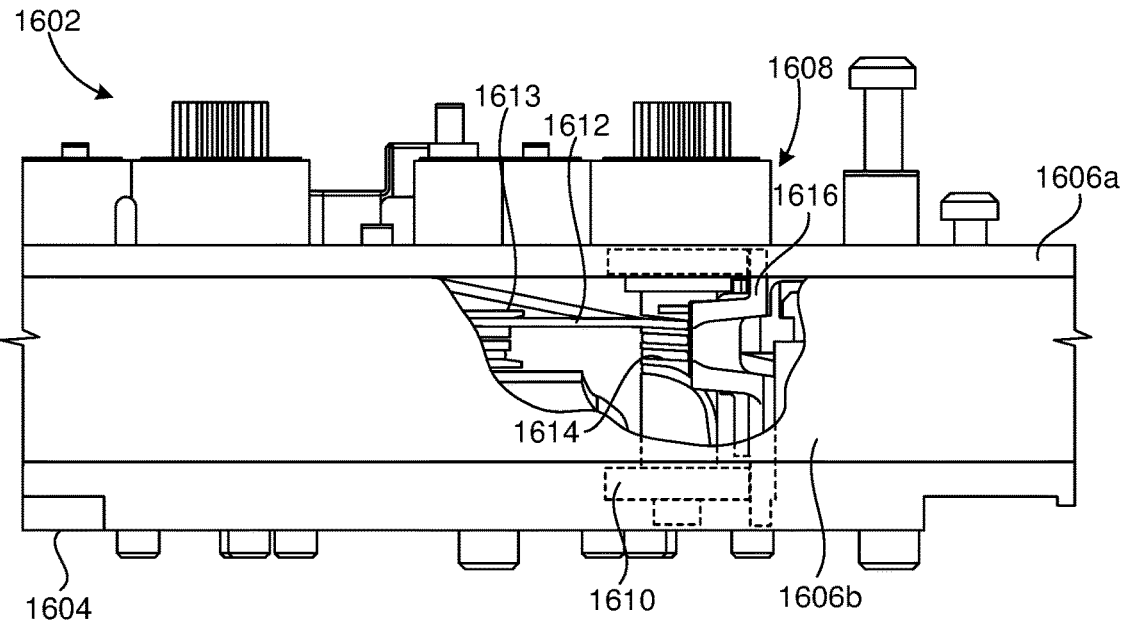
FIG. 16 is a cutaway side view of various internal component parts of another example surgical tool.

FIG. 16 is a cutaway side view showing various internal component parts of another example surgical tool 1602, according to one or more embodiments of the present disclosure. More specifically, FIG. 16 depicts the internal component parts of a drive housing 1604 of the surgical tool 1602. The surgical tool 1602 may be similar in some respects to the surgical tool 600 of FIG. 6 and, therefore, may be best understood with reference thereto.

The drive housing 1604 may provide an upper chassis 1606*a* and a lower chassis 1606*b*, where the upper and lower chassis 1606*a,b* are offset from each other. In some embodiments, however, the lower chassis 1616*b* may form part of the drive housing 1604 itself, without departing from the scope of the disclosure.

At least one drive cable capstan 1608 may be arranged within the drive housing 1604 and positioned for rotation therein. In the illustrated embodiment, the drive cable capstan 1608 is operatively coupled to or otherwise forms an integral part or extension of an input 1610, and actuation of the input 1610 will correspondingly rotate the drive cable capstan 1608.

A drive cable 1612 may be coupled to the drive cable capstan 1608 such that rotation of the drive cable capstan 1608 correspondingly facilitates longitudinal movement of the drive cable 1612. In the illustrated embodiment, the drive cable 1612 is received within a pulley track 1614 and wrapped about the outer circumference of the drive cable capstan 1608 multiple times. The pulley track 1614 is defined on the drive cable capstan 1608 in a helical path, such that the position of the drive cable 1612 within the pulley track 1614 changes elevation as it extends about the circumference of the drive cable capstan 1608. The drive cable 1612 is received by an idler pulley 1613, which redirects the drive cable 1612 into an elongate shaft (not shown) of the surgical tool 1602.

According to the present disclosure, the surgical tool 1602 may further include a capstan guide 1616 arranged within the drive housing 1604 to help prevent derailment of the drive cable 1612 from the drive cable capstan 1608 and, more particularly, from the pulley track 1614. The capstan guide 1616 may be arranged adjacent the drive cable capstan 1608 but offset therefrom such that it does not engage the drive cable capstan 1608 during operation. The capstan guide 1616 may extend between the upper and lower chassis 1606a,b. In some embodiments, the capstan guide 1616 may be fixed or otherwise removably secured to one or both of the upper and lower chassis 1606a,b. In other embodiments, the capstan guide 1616 may be simply secured to one or both of the upper and lower chassis 1606a,b.

Figure 17A:
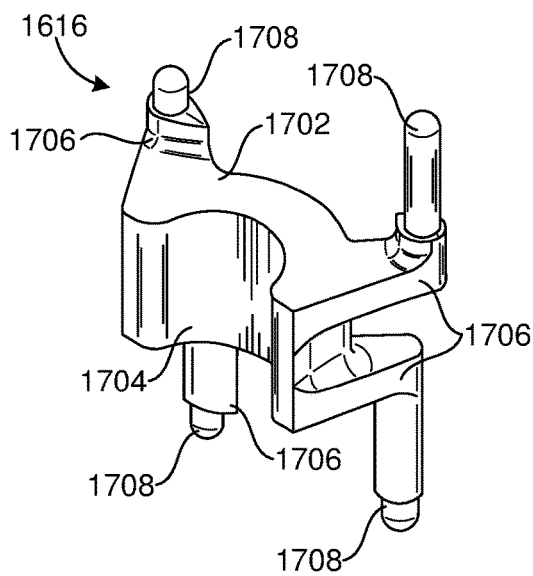
FIGS. 17A and 17B are isometric inner and outer views of the capstan guide of FIG. 16.
Figure 17B:
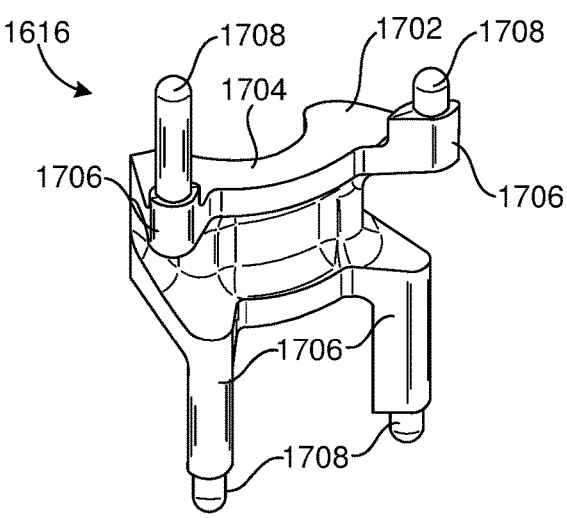

FIGS. 17A and 17B are isometric inner and outer views of an example embodiment of the capstan guide 1616 of FIG. 16, according to one or more embodiments. As illustrated, the capstan guide 1616 includes a guide body 1702 that defines an inner arcuate surface 1704. The inner arcuate surface 1704 may be configured to be positioned adjacent the outer circumference of the drive cable capstan 1608 (FIG. 16) to help maintain the drive cable 1612 within the pulley track 1614 and thereby prevent derailment of the drive cable 1612.

The capstan guide 1616 may also include one or more retention arms 1706 (four shown) extending from the guide body 1702. The retention arms 1706 may be configured to help mount the capstan guide 1616 within the drive housing 1604 (FIG. 16). In at least one embodiment, one or more of the retention arms 1706 may further define or otherwise provide an extension 1708. The extension(s) 1708 may be used to couple the capstan guide 1616 to one or both of the upper and lower chassis 1606a,b. In at least one embodiment, for example, each extension 1708 may be received within a corresponding aperture (not shown) defined in one of the upper or lower chassis 1606a,b. In such embodiments, securing the upper and lower chassis 1606a,b within the drive housing 1604 will correspondingly secure the capstan guide 1616 therein.

By being positioned close to, but not engaging the drive cable capstan 1608 (FIG. 16), the capstan guide 1616 may prove advantageous in helping prevent cable derailment. The capstan guide 1616 does not add any additional friction to the surgical tool 1602 (FIG. 16) and removes the complexity of molding features into the upper and or lower chassis 1606a,b (FIG. 16).

Embodiments disclosed herein include:

A. A surgical tool that includes a drive housing having an input shaft and a drive cable capstan arranged therein, the input shaft including a drive gear and the drive cable capstan including a driven gear intermeshed with the drive gear such that rotation of the input shaft rotates the drive cable capstan, an elongate shaft that extends from the drive housing, an end effector operatively coupled to a distal end of the elongate shaft, and a drive cable received within a pulley track defined on the drive cable capstan and extending only partially around a circumference of the drive cable capstan, wherein the drive cable is fed directly into the elongate shaft from the pulley track and extends to the end effector.

B. A method of operating a surgical tool that includes positioning the surgical tool adjacent a patient for operation, the surgical tool including a drive housing having an input shaft and a drive cable capstan arranged therein, the input shaft including a drive gear and the drive cable capstan including a driven gear intermeshed with the drive gear such that rotation of the input shaft rotates the drive cable capstan, an elongate shaft that extends from the drive housing, an end effector operatively coupled to a distal end of the elongate shaft, and a drive cable received within a pulley track defined on the drive cable capstan and extending only partially around a circumference of the drive cable capstan. The method further including actuating a drive input coupled to the input shaft and thereby rotating the input shaft and the drive cable capstan, feeding the drive cable directly into the elongate shaft from the pulley track, and moving the drive cable longitudinally within the elongate shaft as the drive cable capstan rotates.

C. A drive cable capstan that includes a cylindrical body that defines a cavity, a driven gear provided on an outer radial surface of the body, a pulley track axially offset from the driven gear and defined about a circumference of the body in a single plane to receive a drive cable, and a cable clip that receives the drive cable and is receivable within the cavity to secure the drive cable to the body.

Each of embodiments A, B, and C may have one or more of the following additional elements in any combination: Element 1: wherein the pulley track is defined in a single plane on the drive cable capstan. Element 2: wherein the pulley track is a first pulley track and the drive cable capstan further defines a second pulley track in a single plane and offset from the first pulley track. Element 3: further comprising a cable clip that secures the drive cable to the drive cable capstan. Element 4: wherein the drive cable capstan defines a cavity that receives at least a portion of the cable clip to secure the cable clip to the drive cable capstan. Element 5: wherein the cable clip provides a cable channel and a cable capture orifice that communicates with the cable channel, and wherein an end of the drive cable is received and secured within the cable capture orifice from the cable channel. Element 6: wherein the end of the drive cable is secured within the cable capture orifice with a connector selected from the group consisting of a crimp, a welded attachment, a brazed attachment, an adhesive bond, a mechanical fastener, and any combination thereof. Element 7: wherein the cable channel aligns with the pulley track when the cable clip is coupled to the drive cable capstan. Element 8: wherein the drive cable capstan is one of a plurality of drive cable capstans arranged within the drive housing, and wherein the drive cable is one of a plurality of drive cables and each drive cable is received within a corresponding pulley track defined on each drive cable capstan, and each drive cable extends only partially around a circumference of each drive cable capstan and is fed directly into the elongate shaft from the corresponding pulley track.

Element 9: wherein feeding the drive cable directly into the elongate shaft comprises feeding the drive cable from the pulley track defined in a single plane on the drive cable capstan. Element 10: wherein the pulley track is a first pulley track and the drive cable capstan further defines a second pulley track in a single plane and offset from the first pulley track. Element 11: further comprising securing the drive cable to the drive cable capstan with a cable clip. Element 12: further comprising receiving at least a portion of the cable clip in a cavity defined by the drive cable capstan and thereby securing the cable clip to the drive cable capstan. Element 13: further comprising receiving and securing an end of the drive cable within a cable capture orifice defined by the cable clip. Element 14: further comprising receiving an end of the drive cable within a pulley track defined by the cable clip, and aligning the cable channel with the pulley track when the cable clip is coupled to the drive cable capstan. Element 15: wherein the drive cable capstan is one of a plurality of drive cable capstans arranged within the drive housing, and wherein the drive cable is one of a plurality of drive cables and each drive cable is received within a corresponding pulley track defined on each drive cable capstan, and each drive cable extends only partially around a circumference of each drive cable capstan and is fed directly into the elongate shaft from the corresponding pulley track.

Element 16: wherein the pulley track is a first pulley track and the body further defines a second pulley track in a single plane and offset from the first pulley track. Element 17: wherein the cable clip provides a cable channel and a cable capture orifice that communicates with the cable channel, and wherein an end of the drive cable is received and secured within the cable capture orifice from the cable channel. Element 18: wherein the cable clip provides a center member that secures the drive cable to the cable clip and one or more longitudinally extending legs receivable into the cavity to secure the cable clip to the body.

By way of non-limiting example, exemplary combinations applicable to A, B, and C include: Element 1 with Element 2; Element 3 with Element 4; Element 3 with Element 5; Element 5 with Element 6; Element 5 with Element 7; Element 11 with Element 12; Element 11 with Element 13; Element 11 with Element 14; and Element 17 with Element 18.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee.

Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A surgical tool, comprising:
a drive housing having an input shaft and a drive cable capstan arranged therein, wherein a drive gear is provided on the input shaft and is rotatable therewith and the drive cable capstan includes a driven gear intermeshed with the drive gear such that rotation of the input shaft rotates the drive cable capstan;
an elongate shaft that extends from the drive housing;
an end effector operatively coupled to a distal end of the elongate shaft; and
a drive cable received within a pulley track defined on the drive cable capstan and extending only partially around a circumference of the drive cable capstan, wherein an end of the drive cable is secured to the drive cable capstan and the drive cable is fed directly into the elongate shaft from the pulley track and extends to the end effector.

2. The surgical tool of claim 1, wherein the pulley track is defined in a single plane on the drive cable capstan.

3. The surgical tool of claim 2, wherein the pulley track is a first pulley track and the drive cable capstan further defines a second pulley track in a single plane and offset from the first pulley track.

4. The surgical tool of claim 1, further comprising a cable clip that secures the drive cable to the drive cable capstan.

5. The surgical tool of claim 4, wherein the drive cable capstan defines a cavity that receives at least a portion of the cable clip to secure the cable clip to the drive cable capstan.

6. The surgical tool of claim 4, wherein the cable clip provides a cable channel and a cable capture orifice that communicates with the cable channel, and wherein an end of the drive cable is received and secured within the cable capture orifice from the cable channel.

7. The surgical tool of claim 6, wherein the end of the drive cable is secured within the cable capture orifice with a connector selected from the group consisting of a crimp, a welded attachment, a brazed attachment, an adhesive bond, a mechanical fastener, and any combination thereof.

8. The surgical tool of claim 6, wherein the cable channel aligns with the pulley track when the cable clip is coupled to the drive cable capstan.

9. The surgical tool of claim 1, wherein the drive cable capstan is one of a plurality of drive cable capstans arranged within the drive housing, and wherein the drive cable is one of a plurality of drive cables and each drive cable is received within a corresponding pulley track defined on each drive cable capstan, and each drive cable extends only partially around a circumference of each drive cable capstan and is fed directly into the elongate shaft from the corresponding pulley track.

10. A method of operating a surgical tool, comprising:
positioning the surgical tool adjacent a patient for operation, the surgical tool including:
- a drive housing having an input shaft and a drive cable capstan arranged therein, wherein a drive gear is provided on the input shaft and is rotatable therewith and the drive cable capstan includes a driven gear intermeshed with the drive gear such that rotation of the input shaft rotates the drive cable capstan;
- an elongate shaft that extends from the drive housing;
- an end effector operatively coupled to a distal end of the elongate shaft; and
- a drive cable received within a pulley track defined on the drive cable capstan and extending only partially around a circumference of the drive cable capstan, wherein an end of the drive cable is secured to the drive cable capstan;

actuating a drive input coupled to the input shaft and thereby rotating the input shaft to drive the drive cable capstan;
feeding the drive cable directly into the elongate shaft from the pulley track; and
moving the drive cable longitudinally within the elongate shaft as the drive cable capstan rotates moving the drive cable longitudinally within the elongate shaft as the drive cable capstan rotates.

11. The method of claim 10, wherein feeding the drive cable directly into the elongate shaft comprises feeding the drive cable from the pulley track defined in a single plane on the drive cable capstan.

12. The method of claim 10, wherein the pulley track is a first pulley track and the drive cable capstan further defines a second pulley track in a single plane and offset from the first pulley track.

13. The method of claim 10, further comprising securing the drive cable to the drive cable capstan with a cable clip.

14. The method of claim 13, further comprising receiving at least a portion of the cable clip in a cavity defined by the drive cable capstan and thereby securing the cable clip to the drive cable capstan.

15. The method of claim 13, further comprising receiving and securing an end of the drive cable within a cable capture orifice defined by the cable clip.

16. The method of claim 13, further comprising: receiving an end of the drive cable within a pulley track defined by the cable clip; and aligning the cable channel with the pulley track when the cable clip is coupled to the drive cable capstan.

17. The method of claim 10, wherein the drive cable capstan is one of a plurality of drive cable capstans arranged within the drive housing, and wherein the drive cable is one of a plurality of drive cables and each drive cable is received within a corresponding pulley track defined on each drive cable capstan, and each drive cable extends only partially around a circumference of each drive cable.

18. A drive cable capstan, comprising:
- a cylindrical body that defines a cavity;
- a driven gear provided on an outer radial surface of the body;
- a pulley track axially offset from the driven gear and defined about a circumference of the body in a single plane to receive a drive cable; and
- a cable clip that receives the drive cable and is receivable within the cavity to secure the drive cable to the body.

19. The drive cable capstan of claim 18, wherein the pulley track is a first pulley track and the body further defines a second pulley track in a single plane and offset from the first pulley track.

20. The drive cable capstan of claim 18, wherein the cable clip provides a cable channel and a cable capture orifice that communicates with the cable channel, and wherein an end of the drive cable is received and secured within the cable capture orifice from the cable channel.

21. The drive cable capstan of claim 20, wherein the cable clip provides a center member that secures the drive cable to the cable clip and one or more longitudinally extending legs receivable into the cavity to secure the cable clip to the body.

* * * * *